United States Patent [19]

Clark et al.

[11] Patent Number: 4,563,276

[45] Date of Patent: Jan. 7, 1986

[54] CHROMATOGRAPHIC APPARATUS AND PROCESS

[75] Inventors: Linda A. Clark, Plainfield, N.J.; Luis Soto, New York, N.Y.

[73] Assignee: AT&T Bell Laboratories, Murray Hill, N.J.

[21] Appl. No.: 750,247

[22] Filed: Jul. 1, 1985

Related U.S. Application Data

[63] Continuation of Ser. No. 561,962, Dec. 16, 1983, abandoned.

[51] Int. Cl.$^4$ .............................................. B01D 15/08
[52] U.S. Cl. .................................. 210/198.2; 55/386; 65/30.1
[58] Field of Search ................. 210/656, 198.2; 55/67, 55/386; 65/3.1, 3.2, 30.1, 3.11, 3.12

[56] References Cited

U.S. PATENT DOCUMENTS

| | | | |
|---|---|---|---|
| 4,313,748 | 2/1982 | Macedo et al. | 65/30.1 |
| 4,328,299 | 4/1982 | Beall et al. | 65/30.1 |
| 4,376,641 | 3/1983 | Nestrick et al. | 65/30.1 |
| 4,414,012 | 11/1983 | Suto et al. | 65/30.1 |
| 4,419,115 | 12/1983 | Johnson, Jr. et al. | 65/3.11 |

OTHER PUBLICATIONS

"Preparation of Glass Capillary Columns for Gas Chromatography," *Journal of Chromatography*, M. L. Lee et al., 1980, pp. 235-247.

"High-Purity Fused-Silica Capillary Columns for Gas Chromatography", *Journal of Chromatography*, 243, H. Saito, 1982, pp. 189-206.

The Preparation of Porous Layer Open Tubular Columns Using Powdered Glass as A Binding Agent by Cronin. J. Chromatog., 48(1970), pp. 406-411.

A Rapid Method of Surface Modification of Glass Capillary Columns by Torline, Journal of High Resolution Chromatography, Dec. 1978, p. 301.

Gas Chromatography with Glass Capillary Columns by Jennings, Academic Press of New York, pp. 37-40, 1978.

*Primary Examiner*—John Adee
*Attorney, Agent, or Firm*—Bruce S. Schneider

[57] ABSTRACT

Through the intentional introduction of dopants into a glass structure by utilizing a procedure such as is involved in the modified chemical vapor deposition technique and through subsequent drawing of this structure into capillary tubes, a body is formed that is useful for chromatographic processes. For example, the production of an alumina-doped tube allows selective chromatographic separation of unsaturated organic compounds.

10 Claims, 2 Drawing Figures

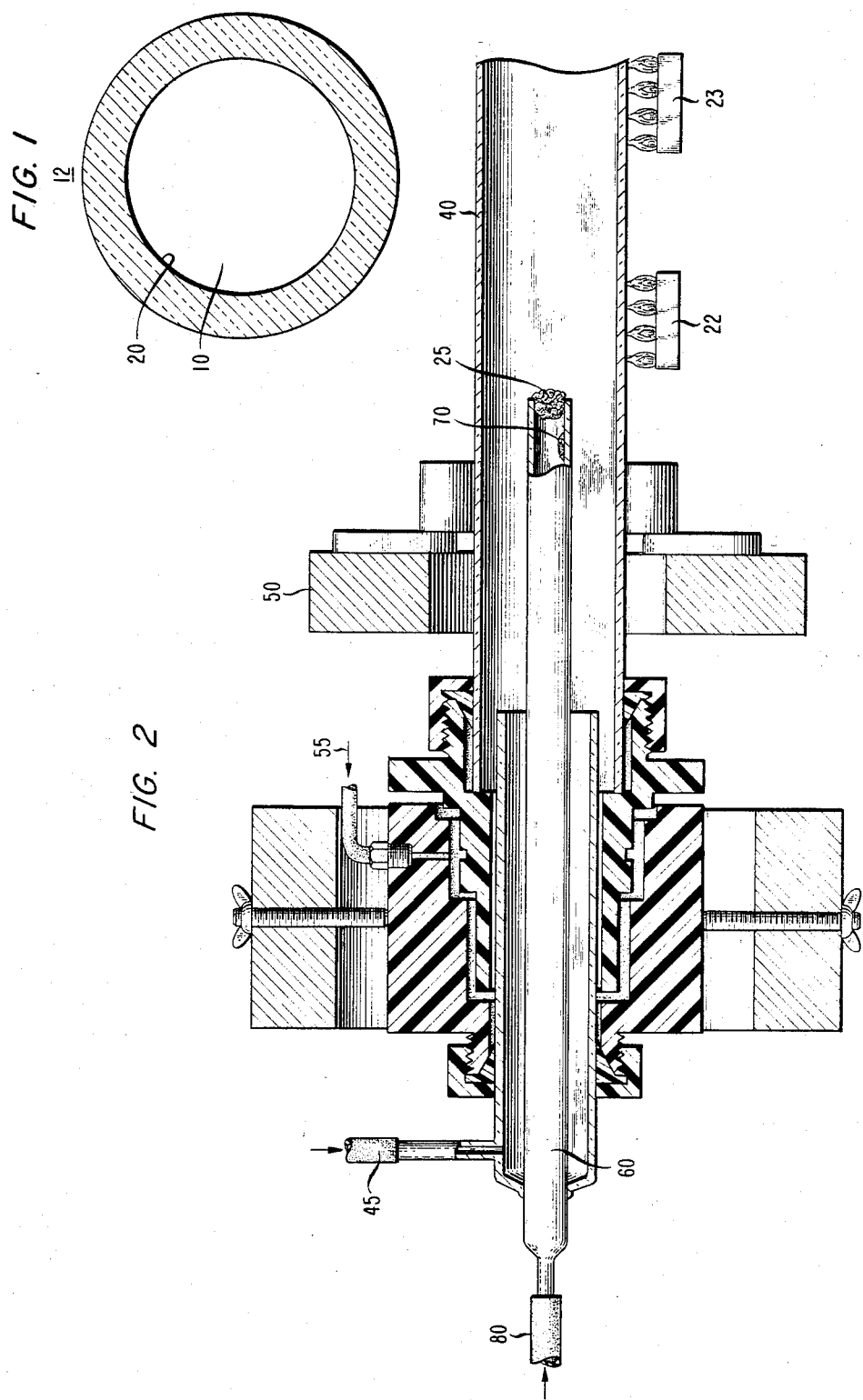

CHROMATOGRAPHIC APPARATUS AND PROCESS

This application is a continuation of application Ser. No. 561,962, filed Dec. 16, 1983, now abandoned.

BACKGROUND OF THE INVENTION

1. Field of the Invention

This invention relates to analytical instruments and, in particular, to chromatographic instruments.

2. Art Background

A variety of chromatographic techniques has been developed for separating mixtures of materials into their components. In one specific technique typically employed for analysis of small quantities, i.e., less than 1 μg, a capillary tube is utilized to affect the desired separation. The mixture is introduced into a flowing gas stream at one end of the capillary tube. Each component of the mixture interacts with the composition at the inner surface of the capillary in a differential manner, and through this differential interaction, each traverses the tube at a characteristic rate. Thus, the mixture is separated into components that sequentially emerge from the tube.

Two general approaches have been employed in capillary chromatography. In the first approach, the differential interaction is provided by adsorption effects between the bore surface and the sample. This approach unfortunately yields poor selectivity and efficiency for all but a few specific components. A second approach involving apparatus modification has been followed in an attempt to improve the selectivity of the separation procedure, i.e., to increase the differences in characteristic migration rates of the components. Generally, this latter approach has involved modification of the capillary tube itself. For example, in one method, the internal surface of the capillary tube is coated with an organic material such as a dimethylsilicone oil or a polyethylene glycol. Separation of the components is produced by a partitioning between the stationary organic coating and the gas flow. The organic coating thus serves to enhance selectivity by yielding a large differential between the interactions experienced by the components of the mixture with the coating. Ideally, the interaction between the bulk material of the capillary tube and the components of the mixture is also entirely eliminated. However, this elimination of interaction, in fact, is rarely achieved.

Capillary tube/mixture interaction is particularly prevalent when metallic capillary tubes, e.g., nickel or copper tubes, are employed. Metals often produce undesirable catalytic degradation of the mixture components and/or of the organic material itself. Additionally, capillary tubes formed from glasses such as borosilicates almost invariably contain impurities. These impurities, such as transition metal oxides and surface hydroxide moieties, often produce irreversible adsorption of sample components and/or degradation of the organic material inner surface coating.

To avoid the difficulties associated with tube/mixture interaction, a variety of expedients is employed to deactivate the tube surface. In a common expedient, the capillary bore is treated first with an intermediate organic layer such as polyethylene glycol, and then the active organic material is applied to the pretreated bore. (See Lee and Wright, *Journal of Chromatography*, 184, 235 (1980), for a description of this and other processes which yield various degrees of deactivation.)

Additionally, in an attempt to avoid the difficulties associated with borosilicate glass, fused quartz capillary tubes have been utilized. This substitution provides a durable, mechanically flexible capillary with lower impurity levels. Nevertheless, low levels of impurities have disadvantages as well as advantages. Some organic coating materials that would potentially yield the desired separation effect do not wet the purer fused silica capillary tube material and thus will not satisfactorily coat the capillary bore walls. To yield adequate wetting and coating stability, surface pretreatment, corresponding to that described for conventional glass tubes, is utilized to enhance the ability of the active material to wet the capillary tube. As an alternative to oil coatings, immobilized polymer films are formed on the capillary surface by in situ cross-linking reactions. (See Lee and Wright supra.) These additional treatments add significantly to the cost and fabrication complexity of the capillary tube.

Thus, the limited selectivity of adsorption chromatography has induced the use of partition techniques when selectivity is desired. However, partition techniques, although quite versatile, require a multi-step treatment leading to greater complexity with associated difficulties and costs.

SUMMARY OF THE INVENTION

Contrary to previous practice, substantially enhanced selectivity for a significantly increased number of components is achievable without the application of an organic layer by uniformly doping the inner surface of a fused silica capillary tube. Additionally, if desired, the wetting by organic compounds of suitable, uniformly doped tubes is achievable without an intermediary layer. This uniform distribution of a dopant, e.g., boron, phosphorus, fluorine, germanium, titanium, or a rare earth composition, is achieved by utilizing a preform fabrication process typically employed for the manufacture of optical fibers as a step in the manufacture of the capillary tube. For example, the preform fabrication process of the modified chemical vapor deposition (MCVD) technique (as described in U.S. Pat. No. 4,217,027, issued Aug. 12, 1980) is employed. In this process, a precursor glass body is produced by forming a glassy material on the interior of a glass tube. This glassy material includes not only silicon compounds such as $SiO_2$ but also a dopant composition containing material such as germanium, boron, and phosphorus in the form of, for example, $GeO_2$, $B_2O_3$, and $P_2O_5$. The precursor body thus produced is then drawn into a capillary tube by well-known techniques such as described in *Optical Fiber Telecommunication*, Chapter 9, "Fiber Drawing and Control," Ed. Miller and Chynoweth, Academic Press, New York (1979). The resulting capillary tube contains a dopant which is relatively uniformly distributed along the walls of the bore. By choosing appropriate dopants and employing this uniform distribution, excellent selectivity is attained without the presence of an active coating. The doped inner surface glass layer has a very low level of undesirable, randomly distributed impurities, e.g., transition metals and hydroxy moieties, that are achievable with presently employed MCVD processes. For example, by the use of an $Al_2O_3$ dopant, it is possible to achieve a more selective separation of materials such as unsaturated hydrocarbons.

BRIEF DESCRIPTION OF THE DRAWING

FIG. 1 is illustrative of capillary tubes involved in the invention; and

FIG. 2 is illustrative of a process involved in the fabrication of such tubes.

DETAILED DESCRIPTION

The invention involves a capillary chromatographic apparatus such as described in *Gas Chromatography With Glass Capillary Columns,* 2nd Edition, Walter Jennings, Academic Press (1980). The capillary tube portion of this apparatus is a fused silica capillary tube having a relatively uniform distribution of dopant material at the surface of the bore. (In this context, a relatively uniform distribution is defined as an excursion of no more than ±5 percent for the average surface dopant concentration over the length of the tube.) The dopant concentration employed, i.e., the average surface concentration of dopant, depends on the selectivity and efficiency desired as well as the particular materials to be separated. A control sample is employed to determine the precise concentration suitable for a desired composition, selectivity, and efficiency. However, an average surface dopant concentration at the surface, 20, of the bore, 10, in the range 50 parts/million to 15 mole percent is generally utilized although in specific situations, dopant levels outside this range are useful. Dopant concentrations of less than 50 parts/million generally yield insignificant enhancement of selectivity, while concentrations greater than 15 mole percent, although not precluded, often lead to fabrication difficulties such as mechanical instability and/or limitations imposed on dopant concentrations by the solubility limits of the dopant in the glass material. (The distance the dopant extends from the bore surface into the body of the capillary tube is not critical since surface interactions are responsible for the desired separation. It is possible to employ capillary tubes doped only at the bore surface or tubes doped throughout the tube body provided the desired bore surface dopant uniformity is maintained.)

The dopant is chosen to yield a selectivity appropriate for the mixture to be separated. For example, dopants containing boron, aluminum, phosphorus, antimony, fluorine, germanium, lead, titanium, zirconium, and the rare earth metals such as europium, neodymium, samarium, and cerium are employable. These dopants are typically advantageously incorporated into the precursor body through the use of volatile reagents such as $POCl_3$ and $GeCl_4$.

Typically these appropriately doped precursor bodies are producible utilizing techniques, in general, employed for the production of optical communication fibers. Although a number of these techniques are available and are not precluded, advantageous results have been achieved utilizing a precursor glass body that is produced by the MCVD method. (See U.S. Pat. Nos. 4,331,462 and 4,217,027, which are hereby incorporated by reference.) This precursor body is drawn by conventional techniques such as described in Chynoweth supra into a capillary tube.

These techniques are adequately described in the cited literature. However, a brief description is included as a pedagogic aid. In particular, a glass tube such as a fused quartz tube having a bore in the range 16 mm to 75 mm is positioned on a glass lathe. A gas flow including a silicon-glass-forming gas, such as silicon tetrachloride, and a dopant glass-forming material, such as $POCl_3$, is combined and introduced into the tube in an oxygen stream. The relative concentration of the dopant glass former to the silicon glass former affects the concentration of the dopant that is present in the final capillary tube. Typically, the ratios by weight of dopant former to glass former in the range 0.07 to 0.25 yield concentrations which are useful. A heating means is then traversed along the axis of the tube to heat its exterior. Generally, this heating means is provided by utilizing a flame which at the external surface of the tube produces a temperature in the range 1300 degrees C. to 2200 degrees C. The heating means is traversed at a rate in the range 1 cm/min to 3 m/min (depending on the heat source) and causes the production of a doped glass region on the bore of the quartz tube. The uniformity of the reagent flow rate and the uniformity of the rate of traversal determine the corresponding uniformity of the dopant distribution in the tube. Typically, to obtain the desired distribution, flow rates and traversal rates should be maintained during the precursor formation process at values that vary no more than 1 percent and 5 percent, respectively. The number of traversals of the tube and the ratio of glass formers regulate the thickness of the doped region in the final capillary tube. A control sample is employed to determine the precise conditions required to produce a desired concentration within a desired doped glass region and thus a desired ultimate surface concentration.

The precursor body is drawn into a capillary, 12, in FIG. 1 as previously discussed. The drawing process is regulated so that the bore, 10, of the capillary tube has an average bore diameter in the range 20 $\mu$m to 1000 $\mu$m, with deviations over the bore length of less than 5 percent. Bores larger than 1000 $\mu$m, although not precluded, generally yield significantly decreased separation efficiency and thus are typically undesirable for most applications. Capillary bores less than 20 $\mu$m, although not precluded, significantly decrease the flow rate at conveniently obtainable pressures thus producing a corresponding increase in the time required for the desired separation. Additionally, more complicated gas handling equipment is utilized for these small diameter bores. Control of the capillary bore size is achieved by controlling the precursor body feed rate and drawing speed during the drawing process. The diameter of bore size is established by a feedback procedure as described in Chynoweth supra.

The separation process of a mixture utilizing the capillaries involved in the subject invention is achieved by introducing the mixture into the capillary tube and inducing it to traverse the tube. The means for introducing the sample, inducing this traversal, and for determining the presence of an eluting component are well known and are described in Jennings supra.

The following examples are illustrative of the subject invention.

EXAMPLE 1

A fused silica tube having an inside diameter of 19 mm and an outside diameter of 25 mm was mounted on a glass lathe. To clean the surface of the bore, a mixture of Freon TM 13 and oxygen (1 l/min of oxygen and 400 cc/min of Freon) was introduced into the tube. An oxyhydrogen torch was traversed along the tube at a rate of 30 cm/min and was adjusted to heat the tube to a temperature in the range of 1800 degrees C. to 2000 degrees C. (as measured with a pyrometer at the external surface of the tube).

After this initial etching treatment, the Freon/oxygen flow was terminated, and a flow containing oxygen and silicon tetrachloride was substituted. This flow was formed by passing 315 cm$^2$/min of oxygen through a silicon tetrachloride bubbler held at 40 degrees C. The flow exiting the bubbler was then combined with an additional 4 l/min flow of oxygen and the combined gas introduced into the tube. The tube was then heated again with an oxyhydrogen torch to approximately 1800 degrees C. by traversing the torch three times across the tube at a rate of approximately 30 cm/min. After each traversal, the flame was extinguished and the torch was returned to the starting position before the next pass was initiated.

The resulting capillary tube precursor was transferred to a drawing tower and drawn into capillary tubing having an internal diameter of approximately 155 μm. The external diameter was controlled by a feedback system described by Chynoweth supra.

EXAMPLE 2

The procedure of Example 1 was followed, except the tube during deposition was maintained at a temperature of approximately 1600 degrees C.

EXAMPLE 3

The procedure of Example 1 was followed, except the gas flow during deposition was modified to produce layers of doped glass. This flow was produced by passing 400 cc/min of oxygen through a silicon tetrachloride bubbler at 40 degrees C. and passing a separate flow of 1000 cc/min of oxygen through a POCl$_3$ bubbler held at approximately 38.8 degrees C. The two oxygen flows exiting from the bubblers were combined and, in turn, combined with an additional 4 l/min flow of oxygen. The tube was heated to a temperature of approximately 1700 degrees C. during the deposition step, utilizing six traversals at 15 cm/min. A capillary tube with an internal diameter of 220 μm was drawn.

EXAMPLE 4

The procedure of Example 3 was followed, except a germanium tetrachloride bubbler rather than a POCl$_3$ bubbler was utilized. The germanium tetrachloride bubbler was maintained at 40 degrees C., and three, rather than six, passes were utilized.

EXAMPLE 5

The procedure of Example 1 was followed, except an aluminum containing dopant was introduced into the deposited glass layer. A tube having a 16 mm internal diameter and a 20 mm external diameter was utilized for this procedure. The deposition gas flow was produced by passing approximately 240 cc/min of oxygen through a silicon tetrachloride bubbler held at 35 degrees C. Additionally, a mixture of 12.5 cc/min of chlorine and 250 cc/min of helium was passed over approximately 10 feet of 0.030 inch diameter aluminum wire confined to a region approximately 80 cm$^3$ in volume, and heated to a temperature of approximately 800 degrees C. The flow from the silicon tetrachloride bubbler and the flow contacting the aluminum were combined with a flow of 3 l/min of oxygen. This combined gas flow was then introduced into the tube and was heated approximately 2100 degrees C., again with an oxyhydrogen torch. Three traversals were employed to produce the deposited layer. A capillary tube having an internal diameter of approximately 280 μm was drawn.

EXAMPLE 6

A deposited layer containing a neodymium dopant was produced following the procedures of Example 1, except the deposition configuration was modified, as shown in FIG. 2, for the particular requirements of introducing the neodymium dopant. In FIG. 2, the deposition tube, 40, measuring 19 mm internally and 25 mm externally, was mounted on the lathe, 50, in a manner so that a second tube, 60, measuring 10 mm internally and 12.5 mm externally, was held concentrically within the deposition tube. Approximately 10 g of neodymium chloride, 70, (99.9 percent pure) was positioned in the internal tube. The neodymium chloride was melted using a torch, 22, by heating it to a temperature of approximately 1000 degrees C. A glass wool plug, 25, was inserted in the end of tube, 60, to prevent NdCl$_3$ particles from reaching the deposition tube. A flow of approximately 1 l/min of helium was passed through tube, 60, through inlet, 80, and a second flow was introduced into the deposition tube through ports, 45 and 55, so that it did not enter the internal tube, 60. This second flow was produced by passing 100 cc/min of oxygen through a silicon tetrachloride bubbler at 35 degrees C. The silicon tetrachloride bearing oxygen was then combined with an additional 1 l/min flow of oxygen. The deposition torch, 23, was then traversed three times at a rate of 20 cc/min and produced a surface temperature of approximately 2000 degrees C. Before the fourth traversal was accomplished, the oxygen flow through the silicon tetrachloride bubbler was terminated, and the helium flow through the internal tube was increased to 1.4 l/min. This final deposition pass was performed to produce a higher concentration of neodymium at the surface of the final capillary tube bore. The bore was approximately 160 μm in diameter.

EXAMPLE 7

For comparison, separations were initially performed on a Hewlett-Packard 5880A gas chromatograph having a capillary injection system and a flame ionization detector. The capillary measured 25 m in length, had a bore size of approximately 0.2 mm, and included an interior 0.33 μm thick coating of cross-linked methylsilicone oil. (The column used is denominated Ultra Performance 19091 A102 by Hewlett-Packard Company.) The injector port was maintained at a temperature of 200 degrees C., the detector was kept at a temperature of 250 degrees C., and the capillary tube was heated to a temperature of approximately 100 degrees C. A helium flow resulting in a 20 psi pressure at the capillary inlet was initiated and maintained. The linear velocity of the helium was 24 cm/sec as measured by a 1.73 min traversal time through the tube for a 10 μl injection of butane. A 4 μl sample of decane, undecane, dodecane, tridecane, and tetradecane at concentrations of 5 mg/ml each in methylene chloride was injected into the capillary tube. Approximately 1.1 percent of this injected sample actually traversed the tube under the conditions of split injection as described in Jennings supra. A second sample was also subsequently injected into the tube. This second sample had a total volume of 1 μl and was a 1 part per thousand solution of 6-chloro-undec-4-ene in methylene dichloride. As a result of these two experiments, a traversal time for the chloroundecene of 23.2 min was measured, while traversal times for the dodecane and tridecane of 14.5 min and 26.5 min, respectively, were measured. The Kovats retention index (Jennings supra, pages 121-126) for the chloroundecene was thus 1277.

EXAMPLE 8

The procedure of Example 7 was followed, except the capillary column utilized was replaced with the alumina-doped capillary whose fabrication was described in Example 5. This column had a length of approximately 22 m and a bore diameter of approximately 0.28 mm. The helium pressure was adjusted to approximately 5 psi, and the butane traversal time under these conditions was 1.49 min, resulting in a linear velocity of 25 cm/sec. During the course of the procedure, the temperature of the column was adjusted from 40 degrees C. to 52.5 degrees C. at a rate of 2.5 degrees C./min. The same samples were introduced as those described in Example 7. The traversal time for the chloroundecene was 3.1 min, while the traversal times for dodecane, tridecane, and tetradecane were 2.1 min, 2.8 min, and 4.1 min, respectively. The Kovats retention index for the chloroundecene was therefore 1331. A comparison of the results obtained in this sample run with that obtained in the previous Example demonstrates a significantly shorter net retention time and a larger retention index for the chlorinated hydrocarbon and thus an interaction that is different in kind from that previously achieved.

What is claimed is:

1. An apparatus for chromatographically separating components of a mixture, said apparatus comprising a fused silica capillary chromatographic structure and means for detecting said components as they emerge from said capillary characterized in that the surface of said capillary bore includes a dopant that is essentially uniformly distributed and that said dopant (1) induces said separation through differential interaction with said components or (2) enhances the wetting of an organic compound that induces said separation through differential interaction with said components.

2. The apparatus of claim 1 wherein said dopant includes a rare earth atom.

3. The apparatus of claim 1 wherein said dopant includes aluminum.

4. The apparatus of claim 1 wherein said dopant comprises phosphorus.

5. The apparatus of claim 1 wherein said dopant comprises germanium.

6. A capillary structure suitable for chromatographically separating components of a mixture comprises a capillary bore surface that includes a dopant that is essentially uniformly distributed in fused silica and that said dopant (1) induces said separation through differential interaction with said components or (2) enhances the wetting of an organic compound that induces said separation through differential interaction with said component.

7. The apparatus of claim 6 wherein said dopant includes a rare earth atom.

8. The apparatus of claim 6 wherein said dopant includes aluminum.

9. The apparatus of claim 6 wherein said dopant comprises phosphorus.

10. The apparatus of claim 6 wherein said dopant comprises germanium.

* * * * *